United States Patent [19]
Pouletty et al.

[11] Patent Number: 5,135,872
[45] Date of Patent: Aug. 4, 1992

[54] MATRIX CONTROLLED METHOD OF DELAYED FLUID DELIVERY FOR ASSAYS

[75] Inventors: Philippe J. Pouletty, Redwood City; Thomas Ingalz, San Jose, both of Calif.

[73] Assignee: Sangstat Medical Corporation, Menlo Park, Calif.

[21] Appl. No.: 345,154

[22] Filed: Apr. 28, 1989

[51] Int. Cl.$^5$ .................. G01N 35/00; G01N 1/10
[52] U.S. Cl. ...................... 436/180; 422/58; 422/61; 422/100
[58] Field of Search .............. 436/180, 177–179; 422/100, 61, 58–59, 56

[56] References Cited

U.S. PATENT DOCUMENTS

| | | | |
|---|---|---|---|
| 4,549,952 | 10/1985 | Columbus | 422/100 |
| 4,855,240 | 8/1989 | Rosenstein et al. | 422/58 |
| 4,868,129 | 9/1989 | Gibbons et al. | 436/179 |
| 4,923,680 | 5/1990 | Nelson | 422/61 |
| 4,960,691 | 10/1990 | Gordon et al. | 422/61 |

FOREIGN PATENT DOCUMENTS

| | | |
|---|---|---|
| 0241611 | 10/1987 | European Pat. Off. |
| 0308232 | 3/1989 | European Pat. Off. |
| 0310862 | 4/1989 | European Pat. Off. |
| 0334015 | 9/1989 | European Pat. Off. |
| 1420916 | 1/1976 | United Kingdom |

*Primary Examiner*—James C. Housel
*Assistant Examiner*—Jan M. Ludlow
*Attorney, Agent, or Firm*—Oblon, Spivak, McClelland, Maier & Neustadt

[57] ABSTRACT

A matrix controlled device having a reservoir having sidewalls and a bottom, and a plurality of conduits positioned in the reservoir and extending through the bottom thereof. Each conduit has an upper opening, a bottom outlet and an optional sidewall opening at a level intermediate the upper level and bottom of the reservoir and the bottom outlet. A flow control matrix plug is positioned in each conduit at a level between the sidewall opening or upper opening, and the bottom outlet. The flow control matrix plug has an internal passageway size which determines the rate at which liquid flows through the plug. By varying the pore density, pore size, dead volume, length, and elevation of the matrix, delay of the flow rate and initial flow of liquid from the respective conduit can be controlled. The size of an upper opening can be reduced to control air flow rates therethrough, and the size and elevation of a sidewall openings can be selected to control liquid flow rates therethrough. The method for delivering a predetermined volume of liquid to a reaction zone is accomplished by introducing liquid into one or more of such conduits, each conduit having a matrix plug therein at a level below the level of liquid introduction. Each matrix individually delays the first release and rate of delivery of the liquid in the conduit.

5 Claims, 11 Drawing Sheets

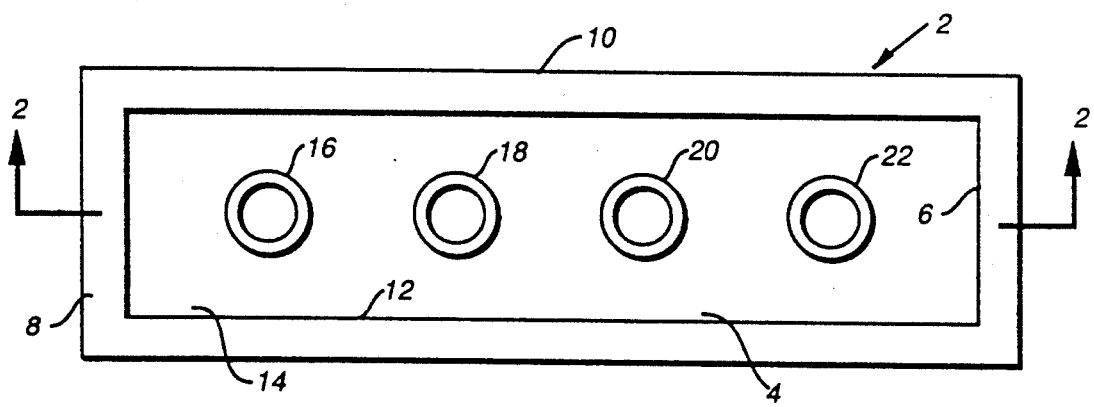
FIG._1
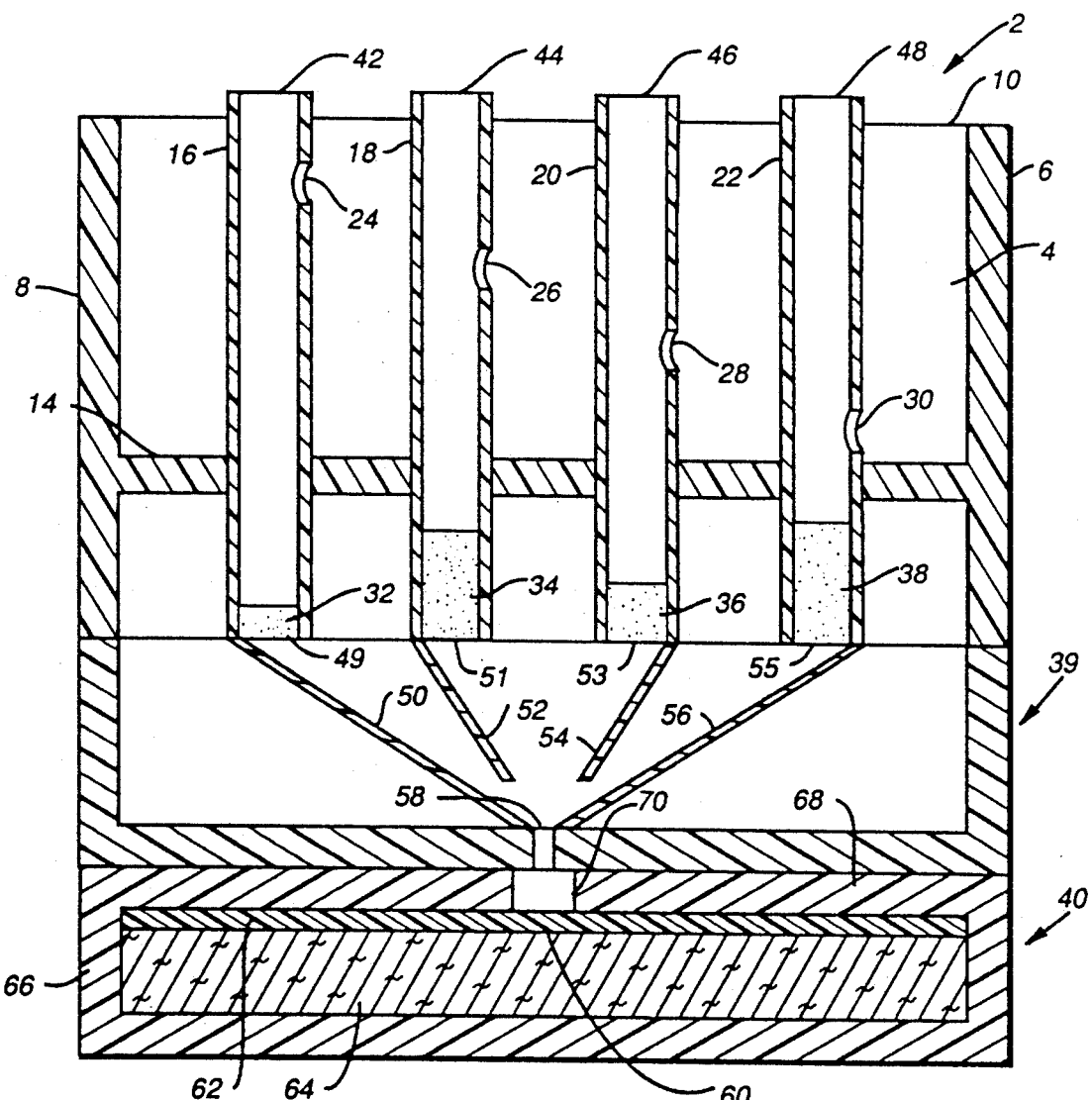
FIG._2

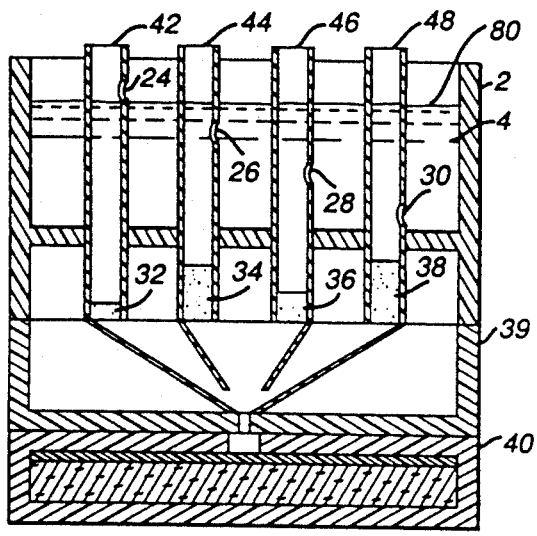
FIG.—3
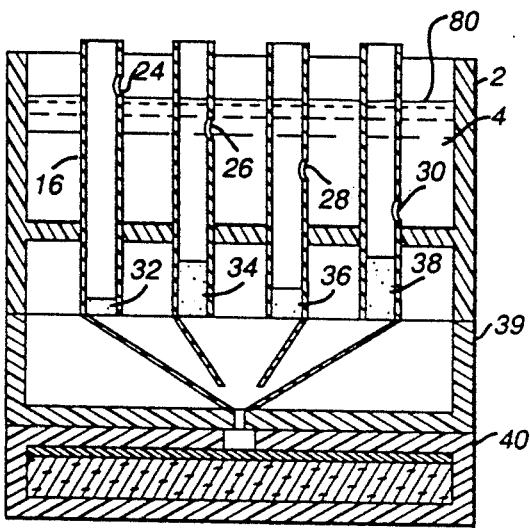
FIG.—4
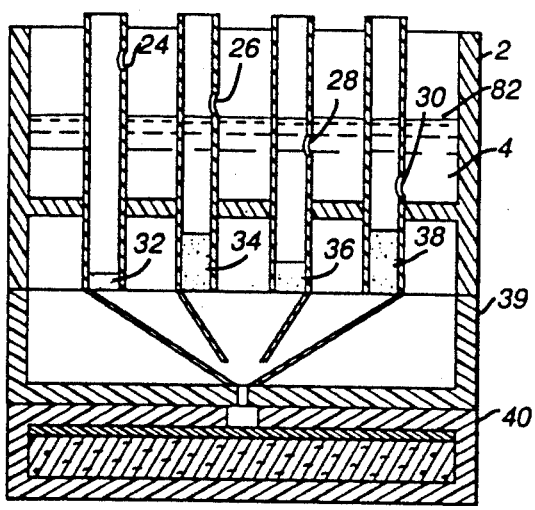
FIG.—5
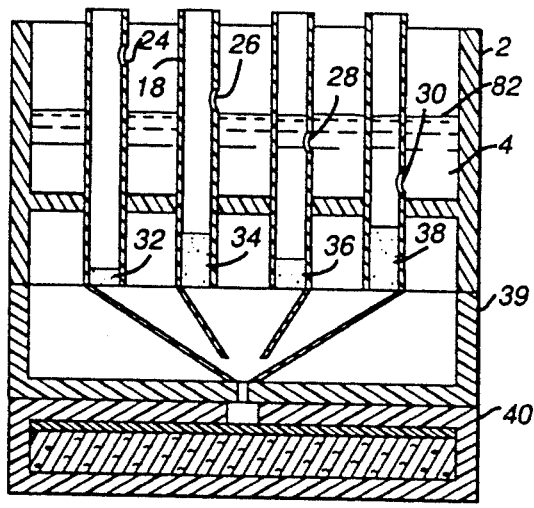
FIG.—6

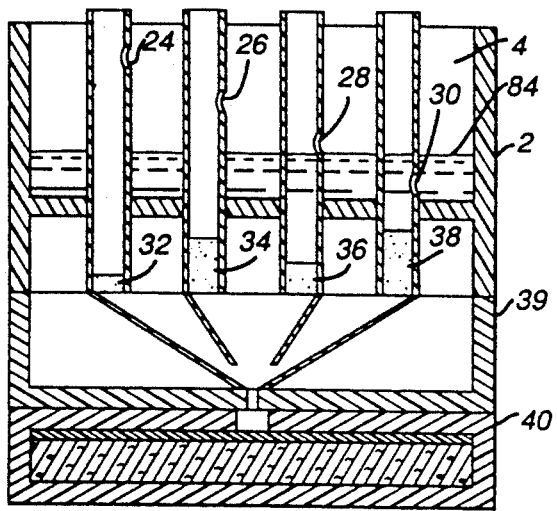
FIG._7
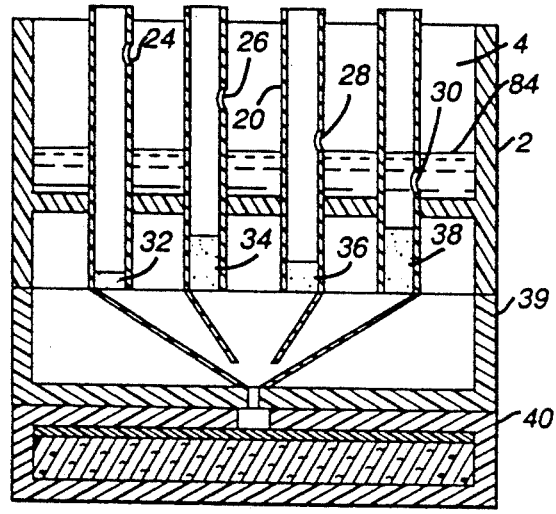
FIG._8
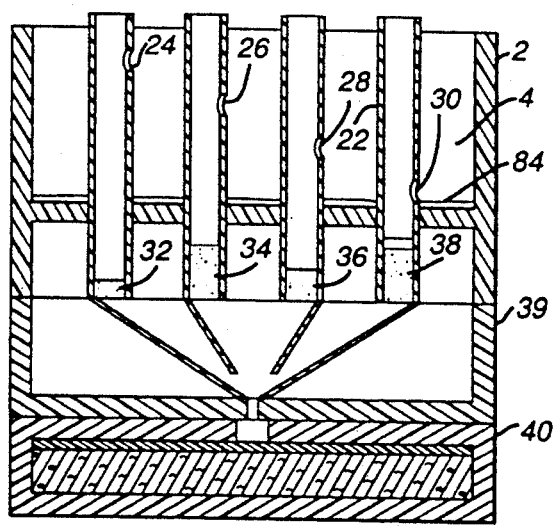
FIG._9

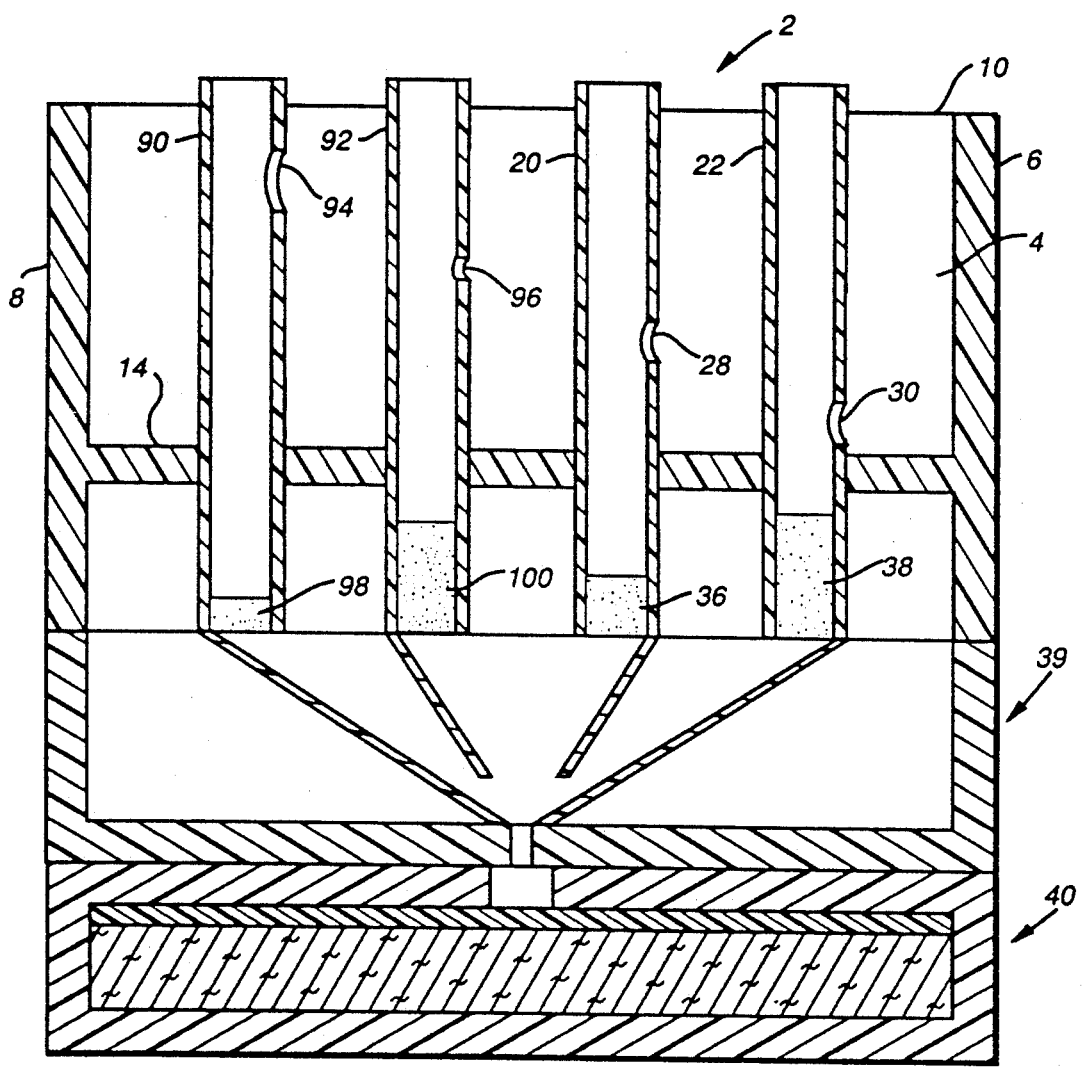
FIG._10

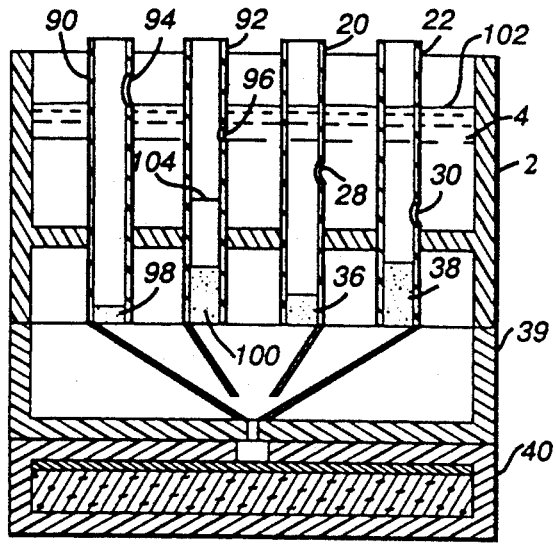
FIG._11
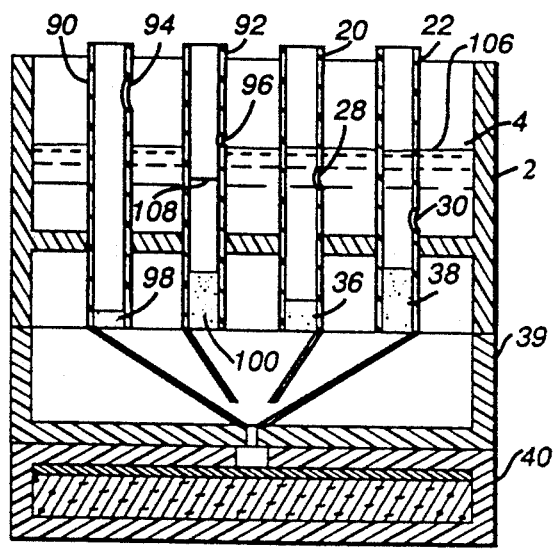
FIG._12
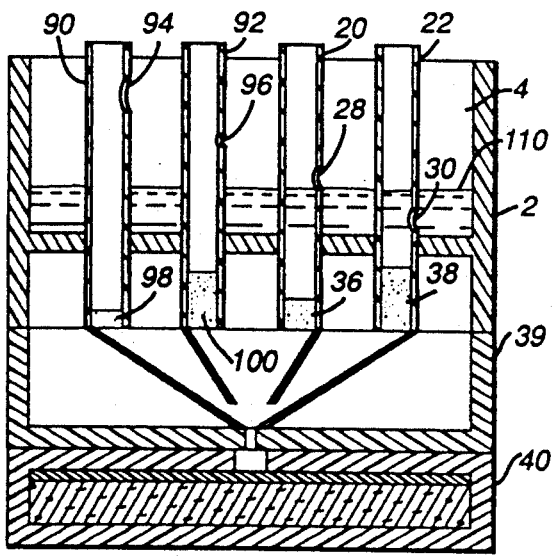
FIG._13
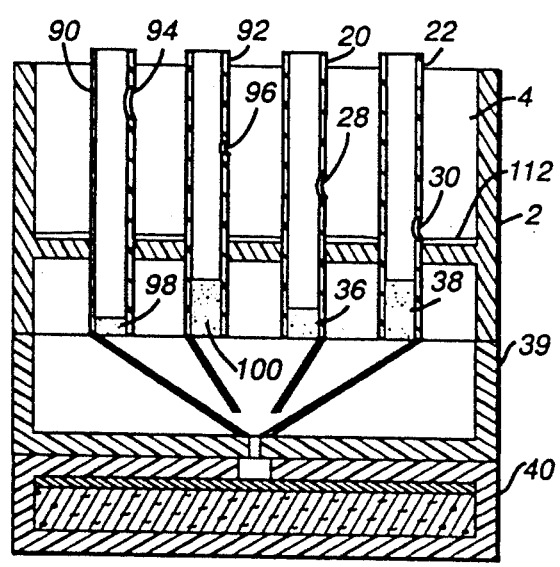
FIG._14

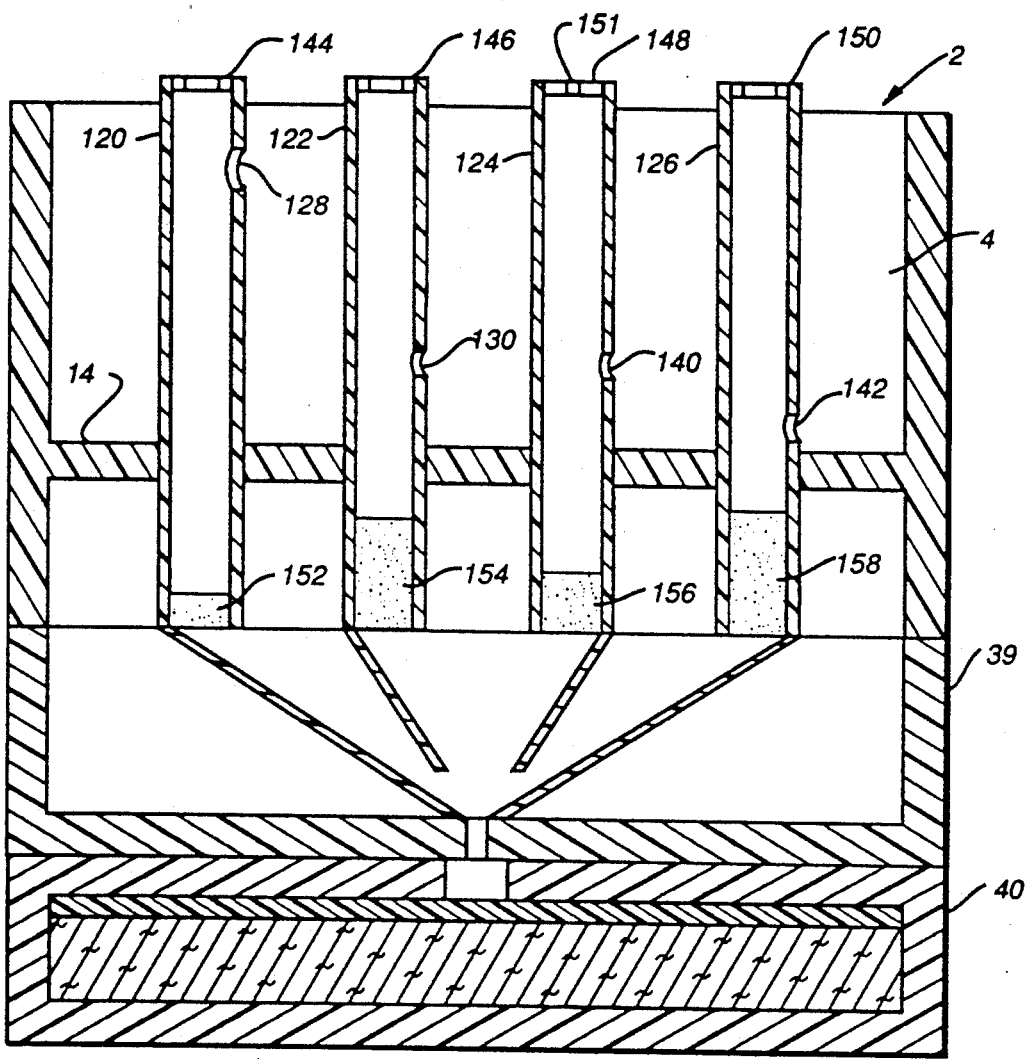
FIG._15

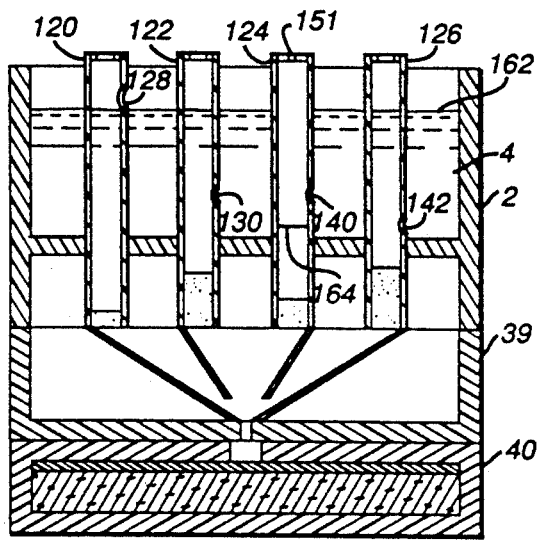
FIG._16
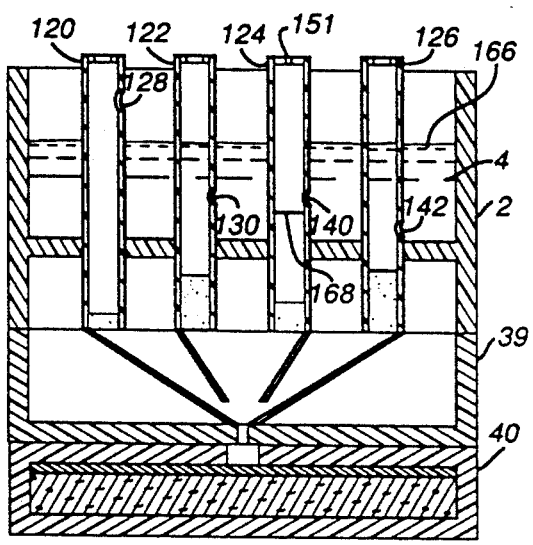
FIG._17
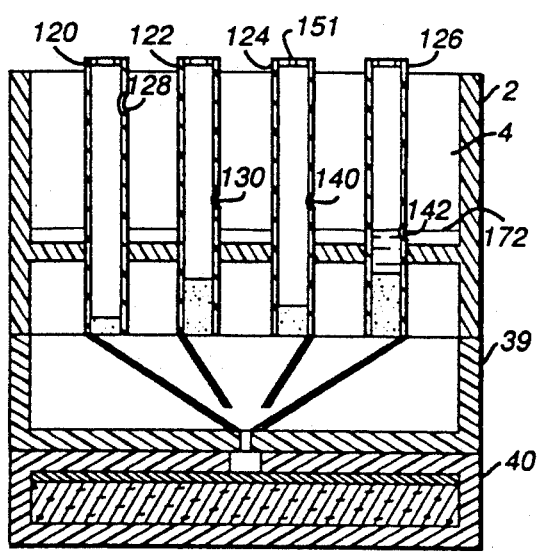
FIG._18
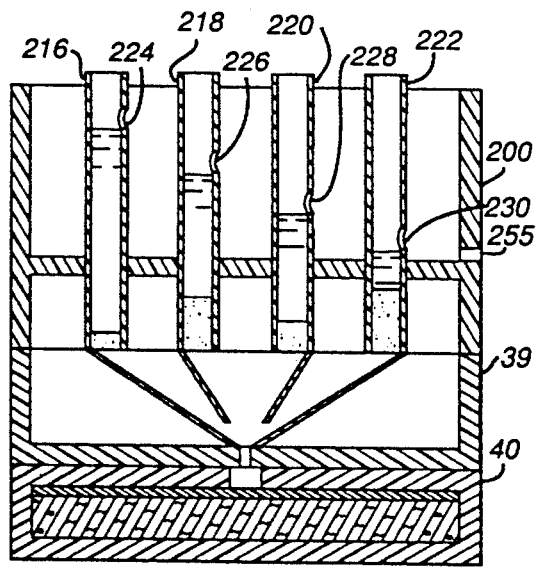
FIG._20

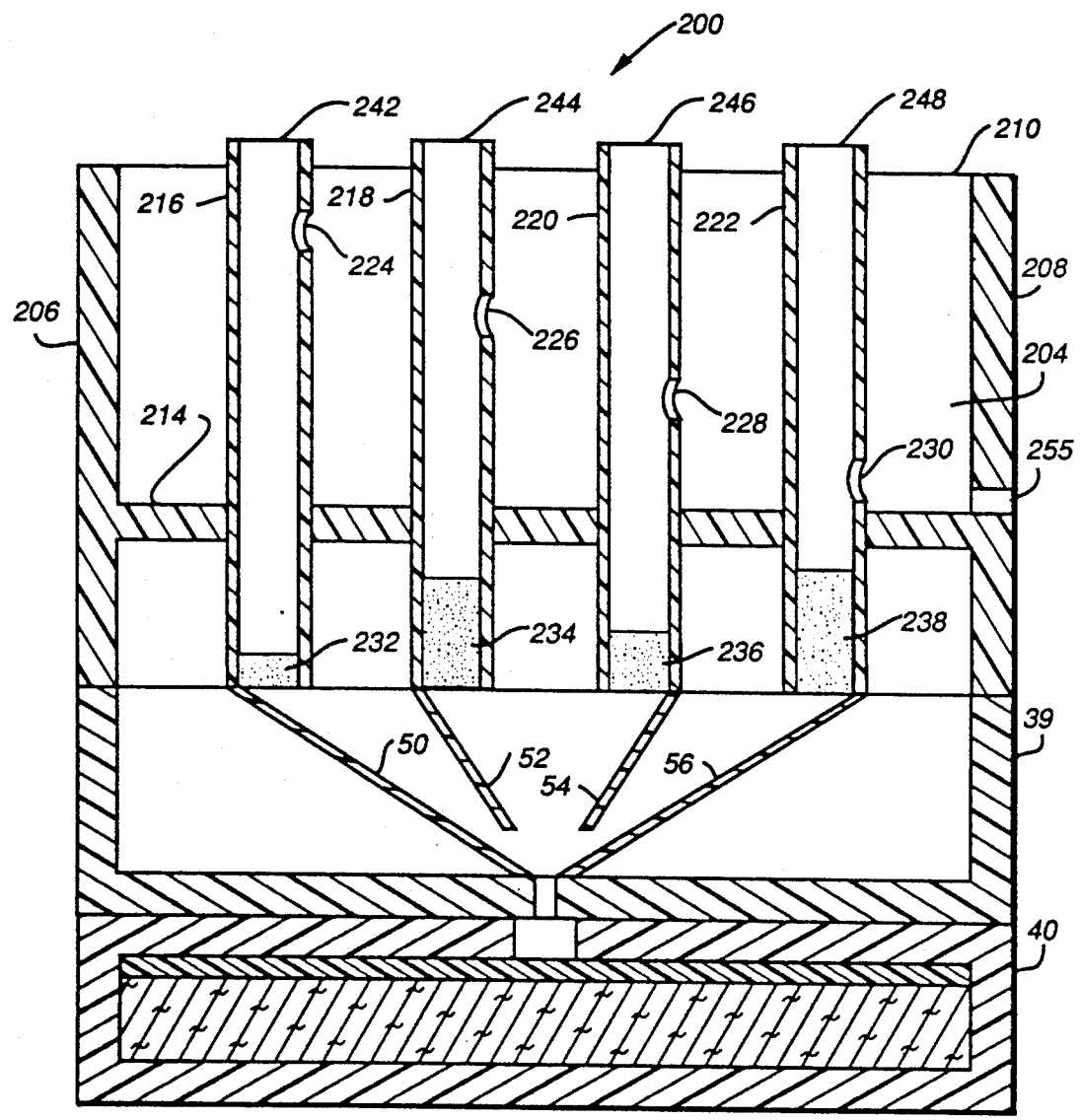
FIG._19

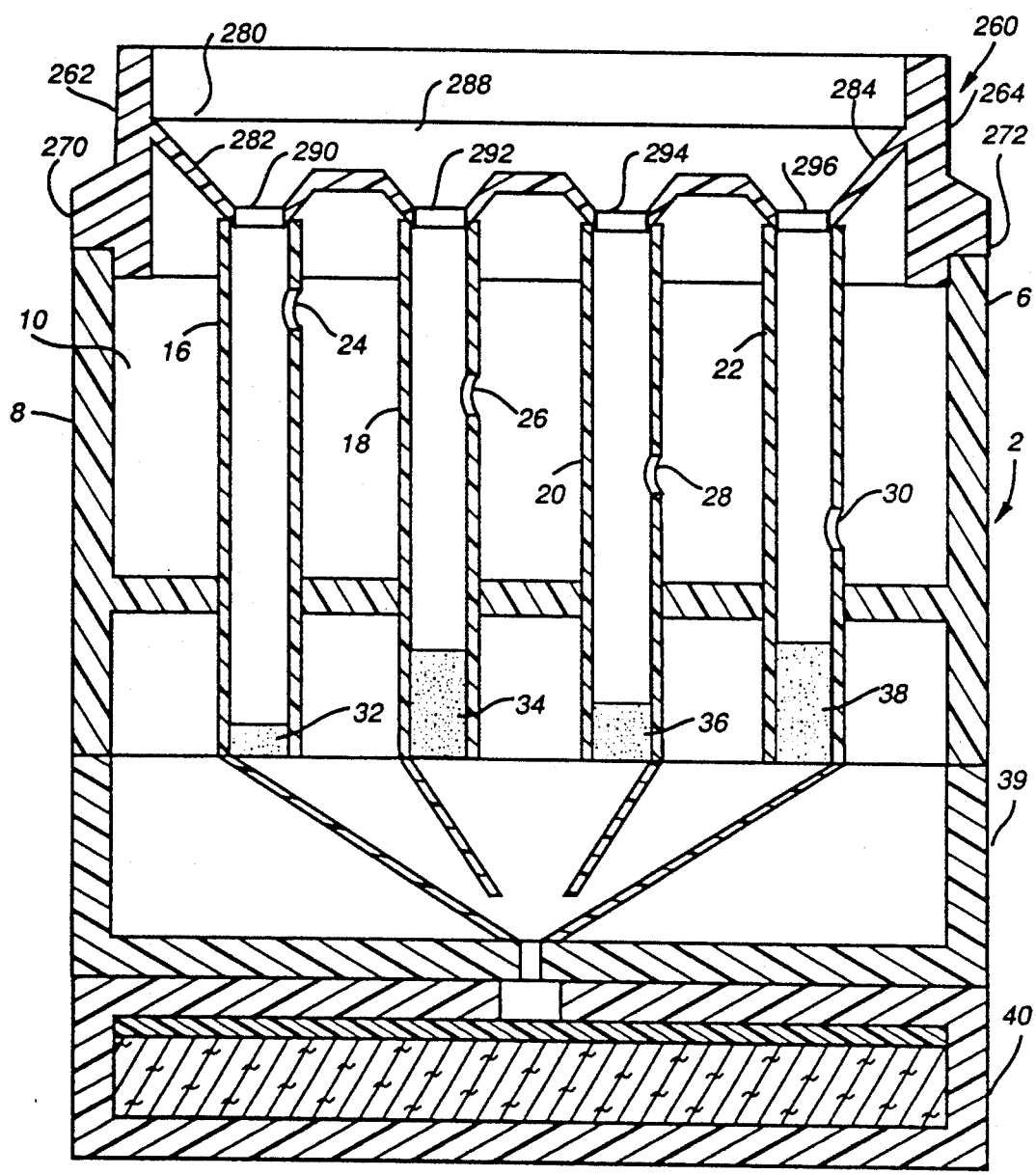
FIG._21
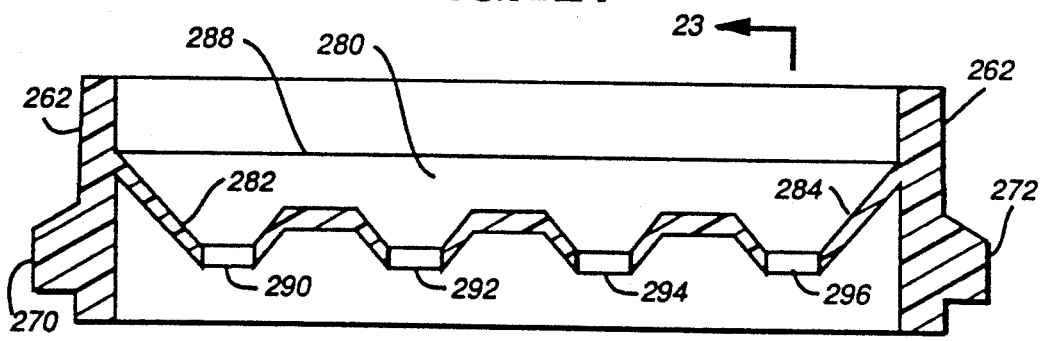
FIG._22

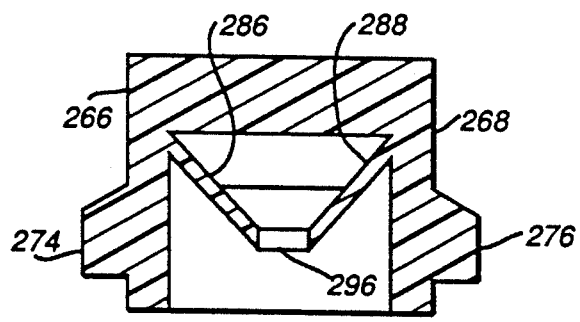
FIG._23
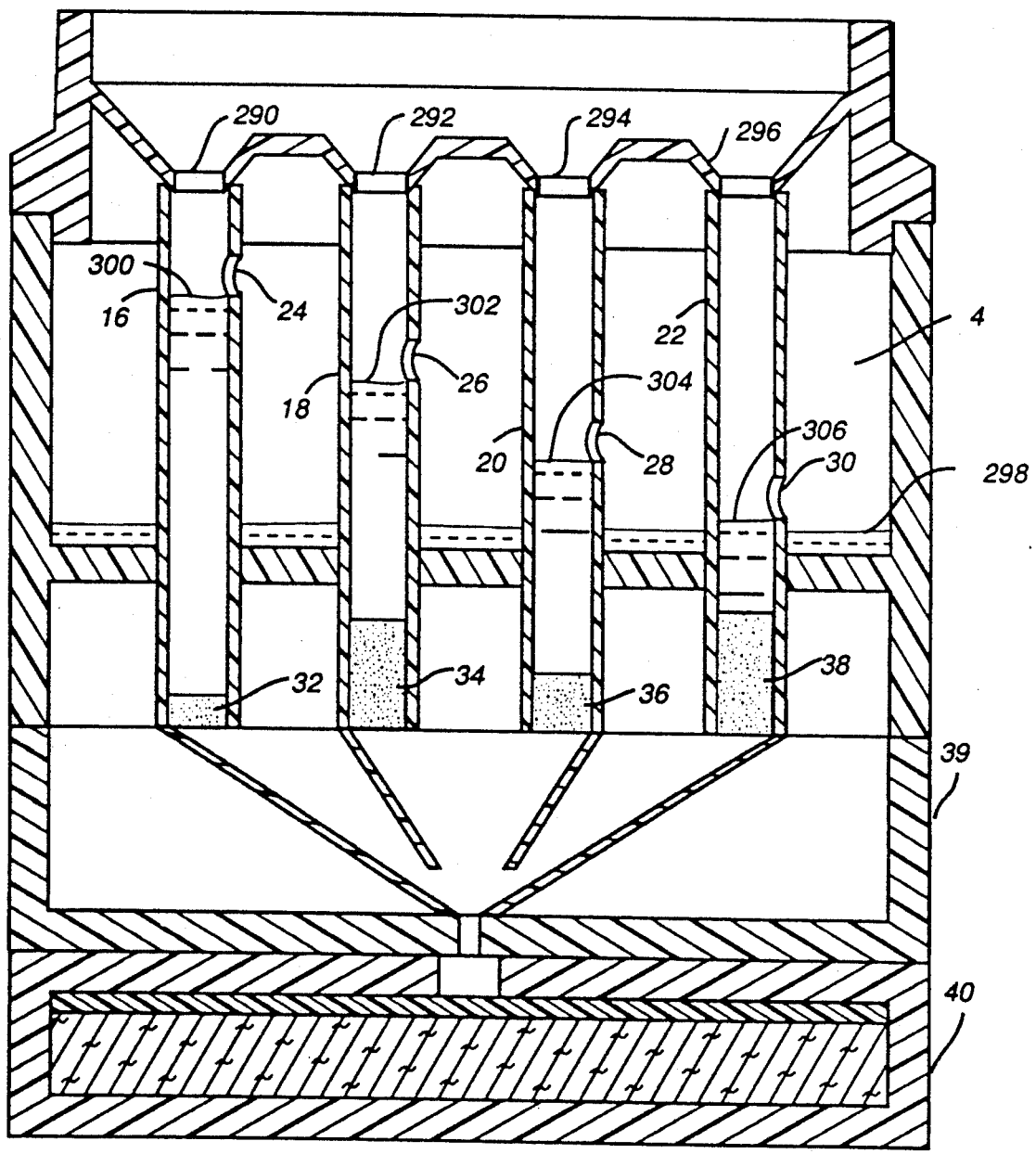
FIG._24

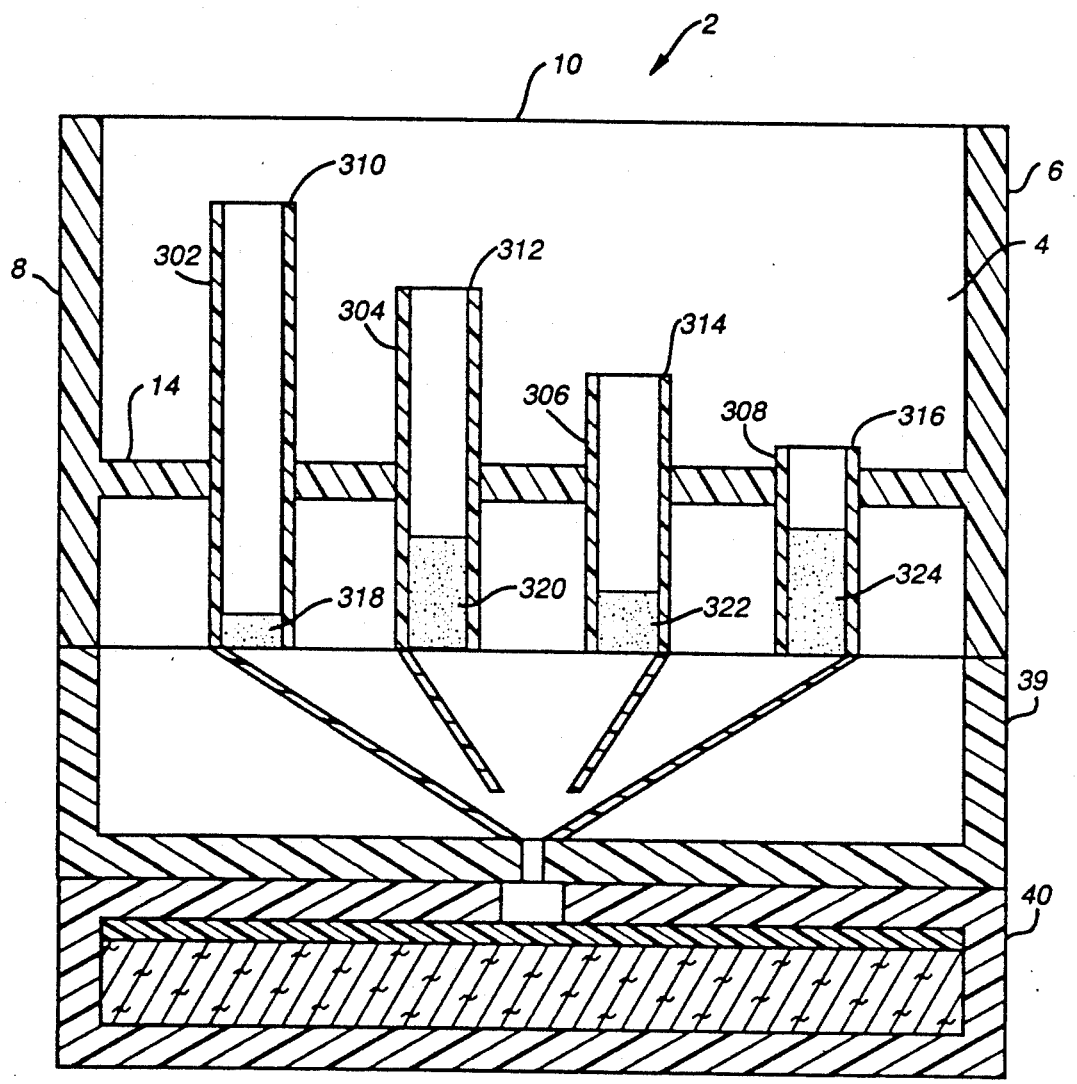
FIG._25

MATRIX CONTROLLED METHOD OF DELAYED FLUID DELIVERY FOR ASSAYS

FIELD OF THE INVENTION

This invention relates to an apparatus and method for carrying out multiple step assays such as immunoassays, clinical chemistry assays and DNA probe assays. In particular, this invention relates to a device which performs a multiple step assay without surveillance, after the clinical technician or other user has added a sample and aqueous medium to the device.

1. Background of the Invention

A wide variety of heterogeneous in vitro assays have been developed and are widely used. They have proven very valuable for detecting or determining the concentration of a wide range of analytes, including antigens, enzymes, nucleic acids, haptens, chemical compounds and the like using properties of antibody/antigen affinity, ligand/receptor affinity, nucleic acid hybridization, enzymatic reactions, and other selective processes. Many of these assays involve reactions between soluble analytes and reagents with a reagent bound to a insoluble phase such as a microtiter well, membrane, porous matrix, bead or the like.

In general, these methods involve a sequence of steps involving interacting the insoluble phase with one or more reagents, often with interspersed washing steps between reactions. These steps can be performed manually be successively adding the various reagents and separating the excess of unbound or unreacted reagent or unwanted reaction product from bound or reacted reagent by washing, precipitation, centrifugation or filtration. Complex automated systems have been developed to perform the same steps.

Recently, integrated rapid immunoassays have been developed using porous membranes or layers containing small beads or activated porous membranes as the insoluble phase and an absorbent collector to capture and retain liquids passing through the membrane. A series of reagents and washing solutions (e.g., clinical sample, antibody or antigen conjugate, washing solutions, chromogenic substrate, or dyed microbeads) are each successively added to the membrane, the liquid phase passing through the membrane and collecting in the absorbent mass. For effective analysis, the reagents must be added in a specific sequence and with specific time intervals to permit a predetermined volume of liquid to pass through the membrane and to permit reactions to occur (incubation).

The membrane techniques are rapid and have proven to be widely applicable in tests required in clinical laboratories, the physician's office and for private use (home tests). The reliability and usefulness of these methods is dependent upon the simplicity of the procedure, particularly when the test is to be used by a person other than a skilled laboratory technician. The higher the number of manual steps, the lower the reliability and convenience. In contrast, high sensitivity and accuracy often requires a higher number of steps such as reactions steps to amplify the detectable signal. Bitin-avidin, biotin-strepavidin, peroxidase-antiperoxidase, enzyme-substrate, and colloidal gold-silver staining reactions are often used to increase sensitivity, for example.

Reagent stability is another factor which is critical for reliable use of tests. Reagents must often remain stable for months after manufacture. Most reagents are most stable in a dry form, and test systems which can readily and easily use reagents in an initially dry form are most desirable.

It can thus be seen that simple, instrument-free tests requiring a minimum of manual steps using dried reagents would be highly desirable.

2. Description of the Prior Art

U.S. Pat. No. 3,888,629 discloses a reaction cell for radioimmunoassays comprising an upper reservoir for holding liquids to be used in the assay reactions, and intermediate matrix pad of absorbent material which can retain necessary reagents for an analytical reaction and a lower absorbent pad to collect liquids after they have passed through the matrix pad. The sample liquid and one or more reagent or wash solutions are added to the upper reservoir in timed sequence, the reactions are carried out in the intermediate matrix, and the matrix examined to determine the test results. A major improvement of this procedure is described in U.S. Pat. No. 4,366,241. The test device is a membrane positioned above an absorbent collector matrix. Reagents such as reagent antibody or reagent antigen, for example, are bound to the membrane and interact with active components of a timed sequence of liquids passed through the membrane. The surface of the membrane is examined to determine the test results. A similar procedure is described in U.S. Pat. No. 4,632,901. Each of these systems require the sequential, timed addition of a series of reagent and wash liquids to the membrane, constant attendance or manual action of a person conducting the test.

A variety of complex, expensive, automated testing systems requiring minimal operator attention have been developed and are used in large central clinical laboratories and high volumes of tests. These are not suitable for use in a small clinical laboratory, doctor's office or home. Simple dip-stick and chemical tests for determining levels of some analytes (such as blood glucose, urine albumin and the like) have been developed which are simple, reliable and do not require manual application of a series of steps. However, these procedures are not adaptable for most assays, and multiple step tests are often required for the level of sensitivity required for a test procedure.

Efforts have been previously made to develop mechanical systems for effecting multiple step test procedures. U.S. Pat. No. 4,665,034 is directed to a multiple syringe system for delivering a sequence of reaction and wash solutions to a reaction area. The operator fully depresses one syringe after the other, in a timed sequence, to deliver sample, reagent and wash solutions to the reaction area. This system, while simplifying, requires constant operator attendance. U.S. Pat. No. 4,673,653 is directed to a unitary device comprising compartments containing reagents and wash solutions with interconnecting channels. When rotated about a horizontal axis, the device delivers by gravity flow, a predetermined sequence and volume of fluids to a reaction zone containing a large bead. U.S. Pat. No. 4,690,801 is directed to another simplified system, wherein the reagent and wash solutions are provided in sealed envelopes. Rotation of an upper element of the assemblage ruptures the envelopes in timed sequence, delivering reagent liquids to a reaction tube.

In each of the simplified systems described above, although volumetric delivery of a series of liquids to a reaction zone is simplified, constant operator manipulation of the device is required. Furthermore, the simplification of demands on the operator is achieved only with the use of a highly complex device or with prepackaged, liquid reagents.

OBJECTS AND SUMMARY OF THE INVENTION

One object of this invention is to provide a compact assay which delivers predetermined sequential or concurrent amounts of reagent liquid to a reaction zone at predetermined times without operator intervention.

It is another object of this invention to provide an inexpensive, disposable assay device, suitable for multistep assays which, after the addition of the sample liquid and assay liquid by the operator, does not require further operator action or attention to produce a test result.

It is a still further object of this invention to achieve the above objects using active reagents which are optionally present in the device in a dry form.

The aforesaid and other objects are achieved by the matrix controlled device and method of this invention. This device comprises a reservoir having sidewalls and a bottom, and a plurality of conduits positioned in the reservoir and extending through the bottom thereof. Each conduit has an upper opening, a bottom outlet and a sidewall opening at a level intermediate the level of the air passage opening and the bottom outlet. A flow control matrix plug is positioned in each conduit at a level between the sidewall opening and the bottom outlet.

The flow control matrix plug has an internal passageway size which determines the rate at which liquid flows through the plug. The flow control matrix plug has a length which, when combined with the internal passageway size, delays initial flow of liquid from the respective conduit through the outlet for a predetermined time.

The size of an upper opening can be reduced to control air flow rates therethrough. The size and elevation of a sidewall openings can be selected to control liquid flow rates therethrough. For embodiments where liquid flows from the reservoir into the conduits, an elevation of a sidewall opening can also be selected to terminate incoming liquid flow from the reservoir when the liquid level in the reservoir falls below that elevation. For embodiments wherein liquid flows directly into the conduits, the elevation and size of a sidewall opening can be selected to permit the escape of excess amounts of liquid from the conduit into the reservoir.

The method of this invention for delivering a predetermined volume of liquid to a reaction zone comprises introducing liquid into a conduit, the conduit having a matrix plug therein at a level below the level of liquid introduction. The matrix delays the first release and rate of delivery of the liquid in the conduit. The volume of liquid delivered by the conduit is predetermined by the size of an upper opening of the conduit, the size and elevation of a sidewall opening in the conduit, and the manner of introducing liquid to the conduit.

The method of this invention for delivering predetermined sequential or concurrent amounts of reagent liquid to a reaction zone at predetermined times comprises the delivery of the volumes from a plurality of conduits. Each conduit has an individually selected matrix plug size and permeability which determines the delay of initial liquid flow from the conduit, and a sidewall opening size and elevation which alone or in conjunction with an upper opening determines the volume of reagent liquid available in the conduit for delivery.

When one or more flow control matrices are impregnated with soluble reagents, delivery preselected, sequential or concurrent volumes of solution containing the respective reagents are effected.

A matrix controlled immunoassay device of this invention comprises a combination of the matrix controlled device and a reaction zone system such as a membrane layer assay device. For example, the membrane layer assay device can comprise a membrane layer to which a assay binding reagent is bound in a contacting relationship with an absorbent means for absorbing and retaining assay solution. The membrane layer has a surface positioned in communication with the solution delivery means, whereby liquid from the solution delivery means is delivered to the membrane layer surface. The membrane layer can be a semipermeable membrane or a layer comprising a plurality of beads. The assay binding reagent can be a member of a binding pair consisting of analyte composition and a substance which binds selectively with the analyte composition.

BRIEF DESCRIPTION OF THE DRAWINGS

FIG. 1 is a top view of the reservoir and conduit combination of this invention.

FIG. 2 is a cross-sectional view of the device of this invention, taken along the line 2-2 in FIG. 1.

FIG. 3 is a cross-sectional view corresponding to FIG. 2 showing first stage liquid levels.

FIG. 4 is a cross-sectional view corresponding to FIG. 2 showing the first stage liquid level, after drainage of liquid from conduit 16.

FIG. 5 is a cross-sectional view corresponding to FIG. 2 showing the second stage liquid level.

FIG. 6 is a cross-sectional view corresponding to FIG. 2 showing the second stage liquid level, after drainage of liquid from conduit 18.

FIG. 7 is a cross-sectional view corresponding to FIG. 2 showing the third stage liquid level.

FIG. 8 is a cross-sectional view corresponding to FIG. 2 showing the third stage liquid level, after drainage of liquid from conduit 22.

FIG. 9 is a cross-sectional view corresponding to FIG. 2 showing the fourth stage liquid level, after drainage of liquid from conduit 24.

FIG. 10 is a cross-sectional view of an alternate embodiment of the device of this invention, using variations in sidewall opening size to accelerate or retard flow of liquid into selected conduits.

FIG. 11 is a cross-sectional view corresponding to FIG. 10 showing the first stage liquid level, after drainage of liquid from conduit 90.

FIG. 12 is a cross-sectional view corresponding to FIG. 10 showing the second stage liquid level.

FIG. 13 is a cross-sectional view corresponding to FIG. 10 showing the third stage liquid level.

FIG. 14 is a cross-sectional view corresponding to FIG. 10 showing the fourth stage liquid level.

FIG. 15 is a cross-sectional view of an alternate embodiment of the device of this invention, using variations in upper opening size to retard flow of liquid into a selected conduit.

FIG. 16 is a cross-sectional view corresponding to FIG. 15 showing the first stage liquid level.

FIG. 17 is a cross-sectional view corresponding to FIG. 15 showing the second stage liquid level.

FIG. 18 is a cross-sectional view corresponding to FIG. 15 showing a third stage liquid level.

FIG. 19 is a cross-sectional view of an alternate embodiment of the device of this invention, using a reservoir drain to prevent continual flow of liquid flow from the reservoir into the conduits after initial filing is completed.

FIG. 20 is a cross-sectional view corresponding to FIG. 19 showing the first stage liquid level.

FIG. 21 is a cross-sectional view of the embodiment of FIG. 2 with a conduit filling cap.

FIG. 22 is a cross-sectional view of the conduit filling cap.

FIG. 23 is a cross-sectional view of the conduit filling cap of FIG. 22, taken along the line 23–23.

FIG. 24 is a cross-sectional view corresponding to FIG. 21 showing the levels of liquid in the device following completion of liquid addition thereto.

FIG. 25 is a cross-sectional view of an alternate embodiment of the device of this invention without conduit sidewall openings and with variations in elevations of the upper openings terminating liquid flow into each conduit at a preset time interval.

DETAILED DESCRIPTION OF THE INVENTION

This invention relates to an apparatus and method for performing in vitro assays which require minimal and simple operator actions. FIG. 1 is a top view of one embodiment of this invention, and FIG. 2 is a cross-sectional view of the device, taken along the line 2–2.

The upper section 2 of the device automatically meters preset volumes from reservoir 4 which is defined by end walls 6 and 8 and sidewalls 10 and 12 and a bottom plate 14. Sample delivery and volume control conduits 16, 18, 20 and 22 are positioned in the reservoir and extend downward through the bottom plate 14. The conduits have respective sidewall ports 24, 26, 28 and 30, the bottom lip of each sidewall port having a size and elevation preselected to provide a controlled liquid delivery as described in greater detail hereinbelow. The bottom of conduits are closed or plugged by flow control matrix plugs, membranes or filters 32, 34 and 36 and 38. Liquid flowing from the flow delay matrices is directed by liquid converging section 39 to a test section 40.

The tops 42, 44, 46 and 48 of respective conduits 16, 18, 20 and 22 are open or closed by a filter to prevent entry of environmental contaminants. If a sample liquid containing undesired solids such as whole blood is to be introduced through a upper opening of a conduit, a suitable filter to remove solids such as cells can be positioned thereon. Alternatively, the prefiltration of the clinical sample can be effected by an adequate filter matrix plug at the bottom of the conduit. The conduit tops in this embodiment preferably extend to an elevation above the top edges of walls 6, 8, 10 and 12. The conduits can have any cross-sectional shape which facilitates construction and controlled liquid flow. They can have a circular, oval, or polygonal cross-section such as a square, rectangular, triangular, and similar cross-section, and have the same or different inner and outer diameters. The conduits should have an upright orientation in use wherein the sidewall ports have an elevation higher than the flow control matrix plugs and the outlet. A vertical orientation is preferred for most used. The flow control openings 24, 26, 28 and 30 can have any cross-sectional shape desired, for example, rectangular slits, or round or oval holes, and have an elevation selected to provide a preselected liquid volume. A single sidewall port per conduit is shown, but more than one can be provided. As will be shown in greater detail below, the volume to be delivered by each conduit can be determined by the elevation and size of the sidewall ports.

The flow delay matrices are critical elements of the device of this invention. They are porous matrices, membranes or filters made of dense open-cell foam or fibrous composition which will accept but will retard liquid flow and are only penetrated by liquid over a predetermined time period. The matrix surface composition should be sufficiently hydrophilic to permit passage of the liquid reagents and wash solutions. The matrices can be made of any material which can satisfy these requirements. The matrix composition and physical characteristics are selected to provide the desired delay in first liquid breach or penetration of the matrix barrier. Alternatively, the flow rate of liquid through a matrix can be adjusted by pretreatment of a matrix material with a viscous organic compound, such as a high molecular weight polymer, which will disperse in the solution and change its viscosity. The rate of flow will thus be reduced, and the transit time of the liquid through the matrix will be extended.

The delay required will vary from test system to test system and specific stage of the test procedure involved with a particular liquid volume, and is determined by both the size of flow passageways in the matrix plug and the plug length. Time delays of from 1 second to 5 minutes or more are possible, for example, by the selection of a respective matrix material and matrix configuration. The matrices are porous bodies which can be constructed in the form of barriers to liquid flow satisfying the flow speed and flow delay requirements of the device. The matrix elements can be made of any organic or inorganic material which is substantially insoluble and unreactive in the test liquids to be metered therethrough. The matrices can be made of fibers made of glass, cellulose, nylon, polyolefins, polyesters or other organic polymers. They can also be made of porous or open-celled foam materials such as polyurethanes, polyolefins (polyethylene, polypropylene, etc.), vinyl polymers such as polyvinyl chloride, polycarbonates, polysulfones, polyesters which have been modified to have hydrophilicity and pore size (pore diameter, pathway length, and pore density) required for a specific, desired flow delay and rate. They can also be membrane layers having the desired properties. One preferred matrix is the macroporous polyethylene POREX ® matrix (R44 and M28, Porex Technologies, Fiarburn, GA) or polyethylene-microporous polyvinyl chloride matrix described in U.S. Pat. No. 4,761,232, the entire contents of which are hereby incorporated by reference. The matrices muse have a construction or configuration which forms a tight seal with the inner wall surface of end of the volume control conduit. Use of round conduit sections and correspondingly dimensioned rods of matrix material can be used. Alternatively, the matrix plugs can be supported in resilient polymer plugs or mounted in resilient annular polymer sleeves which are sized to form a snug fit with the inner surfaces of the conduits.

The matrices can bed used as simple flow delay devices or they can be additionally used as reagent sources, selectively impregnated with reagent which is released into the liquid stream passing therethrough. The reagent impregnated matrices can be prepared by impregnating the matrix composition with an aqueous solution of the desired reagents, preferably before assembly in the volume control conduit. The impregnated matrix composition is then preferably dried or lyophilized for optimum storage stability of the reagents.

The flow delay characteristic of each matrix can be adjusted by using a length of a matrix composition which effects the desired delay, the longer the liquid flow path through the matrix, the longer the delay of the initial liquid flow from the matrix. Alternatively, each matrix composition can be selected from a different composition which provides the initial liquid flow delay. A combination of matrix composition and length can be used to obtain optimum timing sequences for the liquid deliveries from the conduits. Alternatively or in combination with one or more of the above techniques, the porosity of the matrix can be modified by treating the matrix with a solution of an organic polymer. Pretreatment of the matrix with a solution of a viscous water-soluble polymer such as alginate, gelatin, and the like can be to introduce a viscosity modifying agent into the solution as it passes through the matrix, thus modifying the transit time and flow rate of the liquid.

The flow rate of liquid through the matrices is also a function of the respective level of the liquid surface in the reservoir and in the conduit. Thus, by increasing the elevation of the sidewalls and endwalls of the reservoir and increasing the initial liquid level in the reservoir, the flow rates through the matrices can be increased, and the time delays of first delivery through the matrices can be each decreased. By reducing the elevation of liquid added to the reservoir, the opposite effects are achieved in each conduit and matrix.

The lower, outlet opening 49, 51, 53 or 54 of each respective conduit communicates with a respective liquid flow surface 50, 52, 54 or 56 which directs the liquid from the conduits to a central outlet port 58. Outlet port 58 directs the liquid flow to a reaction zone 60 of a test device 40.

One embodiment of test device which can be used with the liquid control system of this invention is shown in FIG. 2. The device comprises a membrane layer 62 positioned on the surface of an absorbent layer 64 for receiving and retaining liquid flowing through the membrane layer. These layers are enclosed in container 66 which can have any configuration needed for containing the elements. If the container includes a top plate 68, an opening 70 is provided to expose the membrane to the outlet 58, the opening 70 defining the reaction zone 60 in the embodiment illustrated. Suitable membrane and absorbent materials for construction of the test device are described in U.S. Pat. Nos. 4,366,241 and 4,632,901, for example, the entire contents of which are hereby incorporated by reference.

The volume control and flow delay function of the embodiment of this invention shown in FIG. 2 is illustrated in FIG. 3 through FIG. 9. The porosity and length of the flow control matrix plugs 32, 24, 35 and 36 have been selected so that the porosity and flow rate of the respective plugs provides a sequenced first delivery of liquid from the tubes in a left to right direction. Matrix plug 32 is the most porous and permits the maximum rate of liquid flow. Matrix plug 34 is less porous than plug 32, providing a slower liquid penetration and slower flow. Matrix plug 36 is even less porous than plug 34, providing an even slower liquid penetration and even slower flow. Matrix plug 38 is the least porous and provides the slowest liquid penetration and slowest flow. These figures illustrate the liquid levels at successive stages of the metering sequence.

FIG. 3 is a cross-sectional view corresponding to FIG. 2 showing first stage liquid levels. Suitable reagent liquid such as buffered solution has been introduced into the reservoir 4 until the liquid level 80 is above level of sidewall port 24 after all of the conduits are filled, the liquid flowing from the reservoir into the conduits through sidewall openings 24, 26, 28 and 30 as the air in the conduits escapes through the top openings 42, 44, 46 and 48. FIG. 4 is a cross-sectional view showing the first stage liquid level, after drainage of liquid from conduit 16. FIG. 5 is a cross-sectional view showing the second stage liquid level 82 at the level of sidewall port 26 and FIG. 6 is a cross-sectional view showing the second stage liquid level, after drainage of liquid from conduit 18. FIG. 7 is a cross-sectional view showing the third stage liquid level 84 at the level of sidewall port 28, and FIG. 8 shows the third stage liquid level, after drainage of liquid from conduit 20. FIG. 9 is a cross-sectional view showing the fourth stage liquid level 86 at the level of sidewall port 30, after drainage of liquid from conduit 22.

The liquid movement is continuous throughout this sequence, not a series of static stages, as the liquids gradually penetrate and pass through the sequence of increasingly more dense and less porous matrices. The first breakthough of liquid from the matrices occurs first through the most porous and less dense plug 32 and then in succession though plugs 34, 36 and 38, in that order. If a wide difference in porosity is selected, the flow from one conduit can terminate before the flow from the conduit can begin. Alternatively, the differences between porosities of certain adjacent plugs can be selected to be less, and the flows from adjacent conduits can be at least partially concurrent.

FIG. 10 is a cross-sectional view of an alternate embodiment of the device of this invention, using variations in sidewall opening size to accelerate or retard flow of liquid into selected conduits. In this embodiment, conduits 16 and 18 shown in FIG. 2 have been replaced by conduits 90 and 92. Conduit 90 has an enlarged sidewall port 94 and an even more porous flow control matrix plug 98. Conduit 92 has a flow restricting sidewall port 96 with a greatly reduced cross-sectional area, and matrix flow control plug 100 is more dense, longer and less porous than matrix flow control plug 98.

FIG. 11 is a cross-sectional view corresponding to FIG. 10 showing the first stage liquid level, after drainage of liquid from conduit 90. As liquid is introduced into the reservoir 4, the excess quickly flows through opening 94 and through the highly porous matrix flow plug 98 until the liquid level 102 is achieved. Because the liquid flow through sidewall port 96 is restricted by the small size of the opening, the liquid level 104 has not reached the same elevation or level as the level 102 in the reservoir and conduits 20 and 22. FIG. 12 is a cross-sectional view showing the second stage liquid level 106 in the reservoir 4. As the liquid level in the reservoir has fallen to the level of port 96, no further liquid enters conduit 92. Because of the restriction in sidewall port 96 and the passage of liquid into the flow control matrix plug 100, the liquid level 108 in conduit 92 has remained below the level 106 of the reservoir. FIG. 13 shows the third stage liquid level 110. By this stage, all liquid has drained from conduits 90 and 92. FIG. 14 is a cross-sectional view showing the fourth stage liquid level 112, by which time all of the liquid has drained from the conduits. As a consequence of the enlarged sidewall port 94, a greater volume of liquid was directed through conduit 90. Because of the reduced size of sidewall port 96, the total volume of liquid directed through conduit 92 was reduced.

FIG. 15 is a cross-sectional view of an alternate embodiment of the device of this invention, having a reduced air vent opening in the cap of one conduit to retard flow of liquid into the respective conduit. In this embodiment, the conduits in the embodiment of FIG. 2 have been replaced with conduits 120, 122, 124 and 126. The sidewall ports 130, 140 and 142 have the same size and are placed at preselected elevations corresponding to the reservoir level at which liquid flow from the reservoir is to terminate. Sidewall port 128 has an enlarged size to permit an increased liquid flow into the conduit 120. In contrast to the previous embodiments, sidewall ports 130 and 140 are positioned at the same elevation. The conduits have upper caps 144, 146, 148 and 150 having openings for escape of air from the conduits during their filing. Caps 144, 146 and 150 have openings which do not significantly restrict air flow from the respective conduits. Cap 148 has a greatly reduced opening 151 which restricts the rate of air flow therethrough. The effects of this configuration on the liquid flow in the system is shown in FIG. 16 through FIG. 18. Flow control matrix plugs 152, 154, 156 and 158 are selected to provide the matrices with a porosity order of 152 greater than 154, 154 greater than 156 and 156 greater then 158.

FIG. 16 is a cross-sectional view corresponding to FIG. 15 showing the first stage liquid level 162 at the elevation of the sidewall port 128. Flow of liquid into conduit 124 is restricted by the restriction of displaced air flow through the restricted opening 151, and as a result, the liquid level at this stage is only 164. FIG. 17 shows an intermediate liquid level 166, liquid from conduit 120 having ended. The level of liquid in conduits 122 and 126 are the same as the reservoir liquid level. The level 168 in conduit 124 is substantially below the reservoir level, because of the continued restriction in air flow from the reservoir. FIG. 18 is a cross-sectional view showing the third stage liquid level 172. All liquid has drained from conduits 120, 122 and 124, and the last remaining liquid is draining from conduit 126.

As with the preceding embodiments, the liquid flow into the flow control matrix plug continues throughout the sequences. The timing of first release of liquid from the conduit is determined by the porosity and length of the respective plugs. The volume ultimately delivered through a conduit is determined by the elevation of the sidewall port (cutoff elevation), the difference in elevation between the sidewall port cutoff elevation and the top of the matrix, the inner diameter of the conduit, the volume of the matrix, and the rate at which liquid flows from the reservoir into the conduit. The volume of the matrix inherently includes a dead volume, the volume of liquid which fills the matrix pores, stays in the matrix and is consequently not delivered to the conduit outlet. The dead volume can be modified by change of the port density and port size of the matrix. By increasing the sidewall port size, the flow rate and ultimate volume of delivered liquid can be increased. By restricting the sidewall port size and/or restricting the size of the displaced air outlet opening, the flow rate of liquid into a conduit can be reduced, limiting the ultimate volume of liquid delivered through the respective conduit.

FIG. 19 is a cross-sectional view of an alternate embodiment of the device of this invention, using a reservoir drain to prevent continual flow of liquid flow from the reservoir into the conduits after initial filing is completed. The upper section 200 of the device automatically meters preset volumes from reservoir 204 which is defined by end walls 206 and 208 and sidewalls 210 and 212 (not shown) and a bottom plate 214. Sample delivery and volume control conduits 216, 218, 220 and 222 are positioned in the reservoir and extend downward through the bottom plate 214. The conduits have respective sidewall ports 224, 226, 228 and 230, the bottom lip of each sidewall port having a size and elevation preselected to provide a controlled liquid delivery as described in greater detail hereinbelow. The bottom of conduits are closed or plugged by flow control matrix plugs 232, 234 and 236 and 238. The tops 242, 244, 246 and 248 of respective conduits 216, 218, 220 and 222 are open or closed by a filter as in the embodiment of FIG. 2. The lower, outlet opening 249, 251, 253 or 254 of each respective conduit communicates with a respective liquid flow surface 50, 52, 54 or 56 as described above with respect to FIG. 2. Drain port 255 placed above the bottom plate 214 drains liquid from the reservoir 202 after the conduits are filled.

FIG. 20 is a cross-sectional view corresponding to FIG. 19 showing the first stage liquid level after the liquid has drained from the reservoir. As the liquid flows into the conduits through the sidewall ports 224, 226, 228 and 230, the liquid also begins to drain out of the reservoir through the drain port 255, and this process continues until the liquid has completely drained form the reservoir 202. The liquid levels remaining in the conduits 216, 216, 220 and 222 are determined by the elevation of the lower lip surface of the respective openings 224, 226, 228 and 230. The fluid flow from the conduits 216, 220 and 222 has not begun at this stage because the liquid portions in the respective conduits have not penetrated and begun to exit from the respective flow control matrix plugs 234, 236 and 238. The volumes of liquid remaining in the conduits 218, 220 and 222 at this stage are thus each substantially predetermined by the size (inner diameter) of the conduit, elevation of the inlet conduit and the position of the top surface of the flow control matrix plug. It will be readily apparent that this volume can be determined to a preselected volume by varying the inner diameter or configuration of the conduit, positioning the inlet opening to a desired elevation, and adjusting the upper surface elevation of the matrix plug. Any one or any combination of these adjustments are considered to be within the scope of this invention.

FIG. 21 is a cross-sectional view of the embodiment of FIG. 2 with a conduit filling cap. In this configuration, the liquid is introduced directly into the conduits through the upper opening, the excess liquid flowing outward through sidewall ports into the reservoir. FIG. 22 is a cross-sectional view of the conduit filling cap and FIG. 23 is a cross-sectional view of the conduit filling cap of FIG. 22, taken along the line 23—23.

The conduit filing cap 260 has end walls 262 and 264 and sidewalls 266 and 268 dimensioned to nest inside of the endwalls 6 and 8, and sidewalls 10 and 12 (not shown) of the reservoir 2. Projections 270, 272, 274 and 278 extend outward from the endwall and sidewalls to rest on the upper edge of the reservoir walls, thus securing the cap in a precise position on the reservoir. The filing cap has a filling volume defined by the sidewalls and endwalls and the funnel plate 280. The funnel plate 280 has tapered surfaces 282, 284, 286 and 288 extending from the walls to drain openings 290, 292, 294 and 296 which are precisely aligned with respective conduits 16, 18, 20 and 22 when the cap is in place.

FIG. 24 is a cross-sectional view corresponding to FIG. 21 showing the levels of liquid in the device following completion of liquid addition thereto. Liquid introduced into the filling cap flows through the drain openings 290, 292, 294, and 296 into the respective conduits until the liquid level in each respective tube rises to the level of the respective sidewall ports 24, 26, 28 and 30. Excess liquid 298 then drains from the sidewall ports into the reservoir 4, leaving liquid levels 300, 302, 304 and 306 in the respective conduits. The fluid flow from the conduits 16, 18, 20 and 22 has not begun at this stage because the liquid portions in the respective conduits have not penetrated and begun to exit from the respective flow delay matrices 32, 24, 36 and 38. The volumes of liquid remaining in the conduits 16, 18, 20 and 22 at this stage are thus each substantially predetermined by the size (inner diameter) of the conduit, elevation of the inlet conduit and the position of the top surface of the flow control matrix plug. It will be readily apparent that this volume can be determined to a preselected volume by varying the inner diameter or configuration of the conduit, positioning the inlet opening to a desired elevation, and adjusting the upper surface elevation of the matrix plug. Any one or any combination of these adjustments are considered to be within the scope of this invention.

FIG. 25 is a cross-sectional view of an alternate embodiment of the device of this invention, without sidewalls, and with variations elevations of the top openings selected to terminate liquid flow into each conduit at a preset reservoir level and present time interval. In this embodiment, the conduits 302, 304, 306 and 308 each have a respective upper opening 310, 312, 314 and 316 which is preselected to terminate liquid flow into the conduit as the liquid level in the reservoir falls to the level of the edge of each inlet opening and lower. In this way, the upper openings with their preselected elevations perform the function of the sidewall ports 24, 26, 28 and 30 in FIG. 2. The volume and timing of the flow of liquid from each conduit is determined by the elevation of the upper opening, difference between the elevation of the upper opening and the upper surface of the respective matrix plugs or filters 318, 320, 322 and 324, the elevation and density of the respective matrix plugs or filters and other factors described above.

This embodiment can be used in methods wherein liquid flows from the reservoir into the conduits, with or without a reservoir drain port, or wherein liquid is introduced directly into the conduits, the surplus overflowing the upper opening edges and into the reservoir.

I claim:

1. A method for delivering at least two predetermined volumes of a liquid to a reaction zone which comprises introducing the liquid into at least first and second conduits each having an outlet communicating with the reaction zone and spaced therefrom, the conduits each having a matrix plug therein at a level below the level of liquid introduction and spaced therefrom, and above the outlet of its respective conduit, each matrix plug delaying the first release and rate of delivery of the liquid from its respective conduit, the matrix plug in the first conduit being different from the matrix plug in the second conduit, such that the first release of liquid from the first conduit is delayed until liquid flow from the second conduit is terminated or until after liquid flow from the second conduit has begun.

2. The method of claim 1 wherein the liquid is introduced into each conduit through a sidewall opening therein, the volume of liquid flowing into each conduit being influenced by the size of the sidewall opening therein.

3. A method for delivering at least two predetermined volumes of a liquid to a reaction zone comprises introducing the liquid into at least first and second conduits each having an outlet communicating with the reaction zone, the conduits each having a matrix plug therein at a level below the level of liquid introduction and above the outlet thereof, each matrix plug delaying the first release and rate of delivery of the liquid from its respective conduit, the matrix plug in the first conduit being different from the matrix plug in the second conduit, such that the first release of liquid from the first conduit is delayed until liquid flow from the second conduit is terminated or until after liquid flow from the second conduit has begun, wherein the liquid is introduced into each conduit through a sidewall opening therein, and the volume of liquid flowing into at least one conduit is determined by the size of an upper opening which restricts the flow of displaced air from the conduit.

4. A method for delivering at least two predetermined volumes of a liquid to a reaction zone comprises introducing the liquid into at least first and second conduits each having an outlet communicating with the reaction zone, the conduits each having a matrix plug therein at a level below the level of liquid introduction and above the outlet thereof, each matrix plug delaying the first release and rate of delivery of the liquid from its respective conduit, the matrix plug in the first conduit being different from the matrix plug in the second conduit, such that the first release of liquid from the first conduit is delayed until liquid flow from the second conduit is terminated or until after liquid flow from the second conduit has begun, wherein the liquid is introduced into each conduit through a sidewall opening therein from a reservoir in which the conduit is positioned, the volume of liquid flowing into at least one conduit being determined by the level of the sidewall opening.

5. A method for delivering at least two predetermined volumes of a liquid to a reaction zone comprises introducing the liquid into at least first and second conduits each having an outlet communicating with the reaction zone, the conduits each having a matrix plug therein at a level below the level of liquid introduction and above the outlet thereof, each matrix plug delaying the first release and rate of delivery of the liquid from its respective conduit, the matrix plug in the first conduit being different from the matrix plug in the second conduit, such that the first release of liquid from the first conduit is delayed until liquid flow from the second conduit is terminated or until after liquid flow from the second conduit has begun, wherein the liquid is introduced into each conduit through an upper opening therein, and the volume of liquid retained in at least one conduit is determined by the level of a sidewall opening in the conduit positioned at an elevation between the upper opening and the matrix plug therein.

* * * * *